US012631552B2

(12) United States Patent
Sun et al.

(10) Patent No.: US 12,631,552 B2
(45) Date of Patent: May 19, 2026

(54) METHOD FOR EFFECTIVELY MEASURING TEAR PROTEIN CONTENT IN SOFT HYDROPHILIC CORNEAL CONTACT LENS

(71) Applicant: SUZHOU 3N BIOLOGICAL TECHNOLOGY CO., LTD, Suzhou (CN)

(72) Inventors: Bixia Sun, Suzhou (CN); Ruichun Sun, Suzhou (CN)

(73) Assignee: SUZHOU 3N BIOLOGICAL TECHNOLOGY CO., LTD, Suzhou (CN)

( * ) Notice: Subject to any disclaimer, the term of this patent is extended or adjusted under 35 U.S.C. 154(b) by 162 days.

(21) Appl. No.: 18/269,576

(22) PCT Filed: Dec. 24, 2021

(86) PCT No.: PCT/CN2021/141070
§ 371 (c)(1),
(2) Date: Jun. 26, 2023

(87) PCT Pub. No.: WO2022/143442
PCT Pub. Date: Jul. 7, 2022

(65) Prior Publication Data

US 2024/0060877 A1 Feb. 22, 2024

(30) Foreign Application Priority Data

Dec. 30, 2020 (CN) .......................... 202011613063.6

(51) Int. Cl.
G01N 21/33 (2006.01)
C07K 1/14 (2006.01)
G01N 1/34 (2006.01)
(52) U.S. Cl.
CPC ............. *G01N 21/33* (2013.01); *C07K 1/145* (2013.01); *G01N 1/34* (2013.01)
(58) Field of Classification Search
CPC ........... G01N 21/33; G01N 1/34; C07K 1/145
See application file for complete search history.

(56) References Cited

U.S. PATENT DOCUMENTS

| | | | |
|---|---|---|---|
| 4,526,178 A | 7/1985 | Opel | |
| 4,670,178 A * | 6/1987 | Huth ................... | C11D 3/38609 |
| | | | 424/94.4 |
| 4,738,790 A | 4/1988 | Miyajima et al. | |
| RE32,672 E * | 5/1988 | Huth ..................... | A61L 12/124 |
| | | | 514/840 |
| 5,418,295 A * | 5/1995 | Bowers .................. | G02B 1/043 |
| | | | 525/327.4 |
| 5,820,696 A | 10/1998 | Kimura et al. | |
| 6,008,170 A | 12/1999 | Tanaka et al. | |
| 6,773,894 B1 * | 8/2004 | Han ..................... | G01N 33/567 |
| | | | 436/536 |
| 2004/0131870 A1 * | 7/2004 | Ketelson .............. | C11D 3/3773 |
| | | | 428/474.4 |
| 2004/0241834 A1 * | 12/2004 | James ................. | H01J 49/0418 |
| | | | 250/288 |
| 2005/0106740 A1 * | 5/2005 | Boyes ...................... | C07K 1/36 |
| | | | 422/400 |
| 2008/0190447 A1 * | 8/2008 | Simonette ............... | A61L 12/08 |
| | | | 134/1 |

(Continued)

FOREIGN PATENT DOCUMENTS

| CN | 1387919 A | 1/2003 |
|---|---|---|
| CN | 1732024 A | 2/2006 |

(Continued)

OTHER PUBLICATIONS

International Search Report and Written Opinion received for International Patent Application No. PCT/CN2021/141070, mailed on Jul. 7, 2022, 14 pages.

Keith et al. "A novel procedure for the extraction of protein deposits from soft hydrophilic contact lenses for analysis", available at "https://pubmed.ncbi.nlm.nih.gov/9154390/" published on May 31, 1997, 1 page.

Powell et al. "Evaluation of Extractants and Precipitants in Tear Film Proteomic Analyses", Optometry and Vision Science, vol. 87, No. 11, Nov. 30, 2010, 14 pages.

Subbaraman et al. "Efficacy of an Extraction Solvent Used to Quantify Albumin Deposition on Hydrogel Contact Lens Materials", Eye & Contact Lens, vol. 35, No. 2, Mar. 31, 2009, 2 pages.

Wen et al. "A Testing Method of Assessing the Protein-Removing Effect of the Contact Lenses' Protein-Removing Care Solution", Chinese Journal of Medical Instrumentation, vol. 30, No. 2, Dec. 31, 2006, 1 page.

(Continued)

*Primary Examiner* — Uzma Alam
*Assistant Examiner* — Gisselle M Gutierrez
(74) *Attorney, Agent, or Firm* — Zhong Law, LLC

(57) ABSTRACT

A method for effectively measuring the tear protein content of a soft hydrophilic corneal contact lens is provided in the present invention. The method comprises: preparing a protein extraction solution by mixing acetonitrile, pure water and trifluoroacetic acid; placing the soft hydrophilic corneal contact lens with protein adsorbed on its surface into the protein extraction solution so that the protein extraction solution separates the protein from the soft hydrophilic corneal contact lens; taking out the soft hydrophilic corneal contact lens from the protein extraction solution; detecting a protein concentration in the protein extraction solution by a micro ultraviolet spectrophotometer to obtain a concentration value of the adsorbed protein on the soft hydrophilic corneal contact lens; and calculating a content value of the adsorbed protein on the soft hydrophilic corneal contact lens based on the concentration value of the adsorbed protein on the soft hydrophilic corneal contact lens and a volume of the protein extraction solution. By means of the method, the tear protein content on the surface of the soft hydrophilic corneal contact lens may be quantitatively and qualitatively detected, thus providing users with experimental test data and ensuring the safety of user consumption and use.

3 Claims, No Drawings

(56) References Cited

U.S. PATENT DOCUMENTS

| | | | | | |
|---|---|---|---|---|---|
| 2008/0300386 | A1* | 12/2008 | Lazarev | .................. | C07K 1/145 |
| | | | | | 530/427 |
| 2010/0175711 | A1* | 7/2010 | Simonette | ................. | B08B 3/12 |
| | | | | | 134/1 |
| 2010/0326484 | A1* | 12/2010 | Wu | ........................... | A61L 2/24 |
| | | | | | 134/140 |
| 2012/0138819 | A1* | 6/2012 | Pugh | .................... | A45C 11/005 |
| | | | | | 250/455.11 |
| 2018/0009842 | A1* | 1/2018 | Chen | ...................... | C07K 1/042 |
| 2018/0292575 | A1* | 10/2018 | Jan | .......................... | G02B 1/18 |
| 2018/0292677 | A1* | 10/2018 | Jan | .......................... | A61L 27/34 |
| 2019/0155054 | A1* | 5/2019 | Jan | ......................... | G02B 1/043 |
| 2020/0355848 | A1* | 11/2020 | Jan | ................... | B29D 11/00865 |
| 2022/0326198 | A1* | 10/2022 | Chang | .................... | G01N 30/06 |
| 2023/0357670 | A1* | 11/2023 | Fang | .................... | C11D 3/0078 |
| 2024/0117433 | A1* | 4/2024 | Inoue | ................. | C12N 15/1093 |
| 2024/0176133 | A1* | 5/2024 | Sun | .......................... | C11D 7/28 |
| 2025/0084122 | A1* | 3/2025 | Hill | .................... | G01N 33/6842 |
| 2025/0099414 | A1* | 3/2025 | Harrison | ................ | A61K 47/64 |

FOREIGN PATENT DOCUMENTS

| | | | |
|---|---|---|---|
| CN | 1732255 | A | 2/2006 |
| CN | 102344488 | A | 2/2012 |
| CN | 107384194 | A | 11/2017 |
| CN | 108710221 | A | 10/2018 |
| CN | 109030669 | A | 12/2018 |
| CN | 110954392 | A | 4/2020 |
| JP | 2003084248 | A | 3/2003 |
| JP | 2003121805 | A | 4/2003 |
| TW | 201729848 | A | 9/2017 |
| WO | 2005012915 | A1 | 2/2005 |

OTHER PUBLICATIONS

Zhang et al., "The Kinetics of in Vitro Lysozyme Deposition on Rigid Gas-permeable Contact Lens for a Short Period", Journal of Clinical Rehabilitative Tissue Engineering Research, vol. 14, No. 3, Jan. 15, 2010, pp. 473-476. English abstract only.

Li et al., "Adsorption of BSA on Hydrogel Containing Silicane", Journal of Xinyang Normal University (Natural Science Edition),vol. 20, No. 2, Apr. 30, 2007, pp. 174-178.

Li, et al., "non-official translation: Analysis of Protein Precipitation on Contact Lenses Made from Two Different Materials", Journal of Clinical Medicine in Practice, vol. 13, No. 4, Dec. 31, 2009, pp. 108-109.

Liu Yi et al., Dynamic Observation of the Elution of Protein Deposits from Soft Contact Lenses, Chin J Ophthalmol 1999, vol. 1, No. 2, dated 1999.

Search report received for Chinese Patent Application 2020116130636, dated Mar. 4, 2026.

First Office Action received for Chinese Patent Application 2020116130636, dated Mar. 6, 2026.

* cited by examiner

METHOD FOR EFFECTIVELY MEASURING TEAR PROTEIN CONTENT IN SOFT HYDROPHILIC CORNEAL CONTACT LENS

RELATED APPLICATION

This application is a National Stage Application of International Application No. PCT/CN2021/141070 filed on 24 Dec. 2021 and claims priority from CN application No. 202011613063.6 filed on Dec. 30, 2020 which are hereby expressly incorporated by reference in their entirety for all purposes.

FIELD OF THE INVENTION

Background of the Invention

The present invention relates to the field of biological protein detection, and particularly relates to a method for effectively measuring a tear protein content of a soft hydrophilic corneal contact lens.

Description of the Related Art

The problem of how to remove protein from a corneal contact lens has troubled the industry for more than half a century, which causes great attention of the optometry and ophthalmology industry in various countries to contact lens wearing safety. China also listed the contact lens into Category III medical devices in 2012 for high-risk management due to the frequent occurrence of corneal infection cases on corneal contact lens. The reasons comprise: the contact lens has a great number of fiber oxygen permeable holes invisible to the naked eyes in material structures, the human eyes secrete a large amount of tear at every moment, the tear contains a large amount of tear protein, the tear protein may be so likely to penetrate into the fiber oxygen permeable holes to cause lens DK value reduction (oxygen permeability) and cause symptoms such as cornea anoxia and oedema, and the problems such as cornea injury, bacterial infection, corneal inflammation, or even visual impairment may be caused for serious conditions.

In order to effectively clear the tear protein on the surface of the contact lens and ensure the eye safety of consumers, various methods for removing tear protein from a surface of a soft hydrophilic corneal contact lens are also provided in the market. However, whether the tear protein is completely and effectively eluted or degraded or not is invisible by naked eyes, a protein detection method is gradually accounted to be developed, so that whether the protein is completely degraded or not is effectively verified through scientific detection. However, a detection method for effective protein removal from a soft hydrophilic corneal contact lens in the market at the current stage has a limitation due to a special structure of crisscrossed oxygen permeable holes inside the soft hydrophilic corneal contact lens, and it is not possible to find a method for directly, effectively and precisely measuring the specific value of adsorbed protein on a soft hydrophilic corneal contact lens. Therefore, the detection result thereof is incomprehensive, only has certain reference significance, and cannot become a professional detection basis for quantitatively and qualitatively detecting the protein degradation degree.

Therefore, there is an urgent need to provide a new technical solution to solve the above problems.

SUMMARY OF THE INVENTION

One of the purposes of the present invention is provide a method for effectively measuring a tear protein content of a soft hydrophilic corneal contact lens to solve the problems in the prior art.

According to one aspect of the present invention, a method for effectively measuring the tear protein content of a soft hydrophilic corneal contact lens is provided. The method comprises: preparing a protein extraction solution by mixing acetonitrile, pure water and trifluoroacetic acid; placing the soft hydrophilic corneal contact lens with protein adsorbed on its surface into the protein extraction solution so that the protein extraction solution separates the protein from the soft hydrophilic corneal contact lens; taking out the soft hydrophilic corneal contact lens from the protein extraction solution; detecting a protein concentration in the protein extraction solution by a micro ultraviolet spectrophotometer to obtain a concentration value of the adsorbed protein on the soft hydrophilic corneal contact lens; and calculating a content value of the adsorbed protein on the soft hydrophilic corneal contact lens based on the concentration value of the adsorbed protein on the soft hydrophilic corneal contact lens and a volume of the protein extraction solution In a further embodiment, the protein extraction solution consists of 50 parts of acetonitrile, 50 parts of pure water and 0.2 part of 100% trifluoroacetic acid.

In a further embodiment, the method for effectively measuring the tear protein content of a soft hydrophilic corneal contact lens of the present invention further comprises: preparing the soft hydrophilic corneal contact lens with adsorbed protein on its surface.

In a further embodiment, the preparing the soft hydrophilic corneal contact lens with adsorbed protein on its surface comprises: preparing an artificial tear solution, incubating the soft hydrophilic corneal contact lens in the artificial tear solution at a constant temperature, and taking out the soft hydrophilic corneal contact lens from the artificial tear solution after completion of incubation; detecting a remaining protein concentration in the artificial tear solution by means of the micro ultraviolet spectrophotometer to obtain a remaining protein concentration value after the soft hydrophilic corneal contact lens is taken out from the artificial tear solution; and Further, the incubating the soft hydrophilic corneal contact lens in the artificial tear solution at a constant temperature comprises: placing 1 ml of the artificial tear solution into a centrifuge tube, placing an unused soft hydrophilic corneal contact lens into the artificial tear solution for constant temperature incubation at 37° C. for 1 day, and taking out the soft hydrophilic corneal contact lens to obtain the soft hydrophilic corneal contact lens with protein adsorbed on its surface.

Further, the obtaining a theoretical concentration value of the adsorbed protein on the soft hydrophilic corneal contact lens by means of calculating the concentration of the adsorbed protein on the soft hydrophilic corneal contact lens based on an original protein concentration value and the remaining protein concentration value in the artificial tear solution comprises: obtaining the theoretical concentration value of the adsorbed protein on the soft hydrophilic corneal contact lens by subtracting the obtained remaining protein concentration value from the original protein concentration value in the prepared artificial tear solution In a further embodiment, the original protein concentration value in the artificial tear solution is 2.2 mg/ml, the remaining protein concentration value is 1.328 mg/ml through detection, the theoretical concentration value of the adsorbed protein on the soft hydrophilic corneal contact lens is 0.872 mg/ml by means of calculation.

Further, the placing the soft hydrophilic corneal contact lens with protein adsorbed on its surface into the protein extraction solution so that the protein extraction solution separates the protein from the soft hydrophilic corneal contact lens comprises: placing 1 ml of the protein extraction solution into the centrifuge tube, and placing the soft hydrophilic corneal contact lens into the centrifuge tube for vibration cleaning to separate the adsorbed protein on the soft hydrophilic corneal contact lens from the soft hydrophilic corneal contact lens. The protein concentration in the protein extraction solution is detected by means of the micro ultraviolet spectrophotometer to obtain the concentration value of the adsorbed protein on the soft hydrophilic corneal contact lens which is 0.805 mg/ml through detection; and the content value of the adsorbed protein on the soft hydrophilic corneal contact lens is calculated by means of the obtained concentration value of the adsorbed protein on the soft hydrophilic corneal contact lens.

In a further embodiment, the method further comprises: obtaining an elution rate of the protein extraction solution on the protein by means of calculation based on the obtained concentration value of the adsorbed protein on the soft hydrophilic corneal contact lens and the theoretical concentration value of the adsorbed protein on the soft hydrophilic corneal contact lens.

In a further embodiment, the obtaining an elution rate of the protein extraction solution on the protein by means of calculation based on the obtained concentration value of the adsorbed protein on the soft hydrophilic corneal contact lens and the theoretical concentration value of the adsorbed protein on the soft hydrophilic corneal contact lens comprises: obtaining the elution rate of the protein extraction solution on the protein by means of a ratio of the concentration value of the adsorbed protein on the soft hydrophilic corneal contact lens to the theoretical concentration value of the adsorbed protein on the soft hydrophilic corneal contact lens, wherein the elution rate of the protein extraction solution on the protein is 92.3% by means of calculation.

Compared with the prior art, the present invention has the following advantages and beneficial effects:

The present invention provides a method for effectively measuring the tear protein content of a soft hydrophilic corneal contact lens. Compared with the prior art, the present invention may solve the problem that the specific content of the adsorbed tear protein of the soft hydrophilic corneal contact lens is difficult to measure. The present invention separates the protein from the soft hydrophilic corneal contact lens through the protein extraction solution. The protein extraction solution may be a solution mixed by acetonitrile, pure water and trifluoroacetic acid, and the protein extraction solution does not take a reaction with a material of the soft hydrophilic corneal contact lens, and does not influence the measuring value of the protein. Therefore, the soft hydrophilic corneal contact lens incubated in the artificial tear solution may be used as a detection sample to be placed into the protein extraction solution for protein extraction and separation through vibration. Then, the protein concentration in the protein extraction solution is detected by means of the micro ultraviolet spectrophotometer, and the content value of the adsorbed protein on the soft hydrophilic corneal contact lens may be obtained by means of simple calculation on the protein concentration. Therefore, the specific content of the adsorbed tear protein on the soft hydrophilic corneal contact lens can be obtained by the method of the present invention. Further, the elution rate of the protein extraction solution on the protein may also be obtained by means of experiment detection calculation. Experiment results show that by using this method, the elution rate of the adsorbed tear protein on the soft hydrophilic corneal contact lens is higher than 90%.

DETAILED DESCRIPTION OF THE PREFERRED EMBODIMENTS

The following clearly and completely describes the technical solutions of the present invention in combination with the examples of the present invention. Apparently, the described examples are merely some of the examples of the present invention rather than all of the examples. All other examples obtained by those of ordinary skill in the art based on the disclosed examples without creative efforts shall fall within the protection scope of the present invention.

In descriptions of the present invention, it should be understood that unless otherwise specified and limited, terms should be understood as the general meanings, and those of ordinary skill in the art may understand the specific meanings of the terms in the present invention according to specific situations.

The present invention will be further described below with reference to embodiments.

Embodiments

It is not possible to find a method for directly, effectively and precisely measuring the specific value of adsorbed tear protein on a corneal contact lens in the prior art. In practical application of proving the cleaning effect of the corneal contact lens, there is an urgent need of a test method capable of directly, specifically and quantitatively measuring the adsorbed tear protein on the corneal contact lens. Therefore, in order to solve this problem, the present invention provides a method for effectively measuring the tear protein content of a soft hydrophilic corneal contact lens. The method has a main principle that the adsorbed tear protein on the surface of the soft hydrophilic corneal contact lens and in inside oxygen permeable holes can be extracted 100% according to a protein extraction solution of acetonitrile, trifluoroacetic acid and water. The method detects the protein concentration in the protein extraction solution for the soft hydrophilic corneal contact lens by means of a micro ultraviolet spectrophotometer. The method comprises following operations.

An artificial tear solution is prepared according to a human eye environment, and the soft hydrophilic corneal contact lens is incubated in the artificial tear solution at a constant temperature. After the incubation is completed, the soft hydrophilic corneal contact lens is taken out from the artificial tear solution. A remaining protein concentration in the artificial tear solution is detected by means of the micro ultraviolet spectrophotometer to obtain a remaining protein concentration value. The soft hydrophilic corneal contact lens will absorb the protein when the soft hydrophilic corneal contact lens is incubated in the artificial tear solution at a constant temperature. Therefore, one purpose of the incubation for a period of time is to simulate an application scene of human eyes wearing the soft hydrophilic corneal contact lens. The concentration of the adsorbed protein on the soft hydrophilic corneal contact lens is calculated through an original protein concentration value and the remaining protein concentration value in the artificial tear solution to obtain a theoretical concentration value of the adsorbed protein on the soft hydrophilic corneal contact lens. This is to quantify the protein content on the soft hydrophilic corneal contact lens to assist the subsequent test calculation process. It should be noted that, a well-known substance capable of being used for extracting protein at a current stage is a pbs solution (phosphate buffered solution, a standard salt solution). However, it also has a defect that the protein on the soft hydrophilic corneal contact lens cannot be sufficiently extracted. Therefore, there is no acknowledged method capable of being used for detecting the content of practically adsorbed protein on the soft hydrophilic corneal contact lens worn on human eyes. However, in order to prove the effectiveness of the method of the present invention, the soft hydrophilic corneal contact lens incubated in the artificial tear solution is used for an experiment. On the premise that there is no method for specifically measuring the content of practically adsorbed protein on the soft hydrophilic corneal contact lens, it is default in the experiment that the actual content of the adsorbed protein on the soft hydrophilic corneal contact lens incubated in the artificial tear solution is a theoretical content of the adsorbed protein on the soft hydrophilic corneal contact lens obtained by means of calculation.

A protein extraction solution is prepared. The protein extraction solution comprises acetonitrile, pure water and trifluoroacetic acid. The protein extraction solution does not take a reaction with a material of the soft hydrophilic corneal contact lens, and can separate the protein from the soft hydrophilic corneal contact lens.

The soft hydrophilic corneal contact lens incubated in the artificial tear solution is placed into the protein extraction solution, and the protein is separated from the soft hydrophilic corneal contact lens through the protein extraction solution. The soft hydrophilic corneal contact lens is taken out from the protein extraction solution, protein is dissolved in the protein extraction solution, and the protein concentration in the protein extraction solution is detected by means of the micro ultraviolet spectrophotometer to obtain a concentration value of the adsorbed protein on the soft hydrophilic corneal contact lens.

In one embodiment, the protein extraction solution may be a solution prepared by mixing 50 parts of acetonitrile, 50 parts of pure water and 0.2 part of 100% trifluoroacetic acid.

For example, the concentration of the artificial tear solution prepared according to the human eye environment is 2.2 mg/ml, and the original protein concentration value of the artificial tear solution is 2.2 mg/ml.

In one embodiment, the operation that the soft hydrophilic corneal contact lens is incubated in the artificial tear solution at a constant temperature may specifically comprise the following operations.

Firstly, 1 ml of the artificial tear solution are placed into a centrifuge tube, then, an unused soft hydrophilic corneal contact lens is placed into the artificial tear solution for constant temperature incubation at 37° C. for 1 day, and the unused soft hydrophilic corneal contact lens may be a type IV soft hydrophilic corneal contact lens classified by Food and Drug Administration (FDA).

After incubation of the soft hydrophilic corneal contact lens in the artificial tear solution is completed, the soft hydrophilic corneal contact lens is taken out from the artificial tear solution. The remaining protein concentration in the artificial tear solution is detected through the micro ultraviolet spectrophotometer to obtain the remaining protein concentration value. For example, the remaining protein concentration value is 1.328 mg/ml through detection.

In one further embodiment, the operation that the concentration of the adsorbed protein on the soft hydrophilic corneal contact lens is calculated based on the original protein concentration value and the remaining protein concentration value in the artificial tear solution to obtain a theoretical concentration value of the adsorbed protein on the soft hydrophilic corneal contact lens specifically comprises: the theoretical concentration value of the adsorbed protein on the soft hydrophilic corneal contact lens is obtained by subtracting the obtained remaining protein concentration value from the original protein concentration value in the prepared artificial tear solution. For example, the theoretical concentration value of the adsorbed protein on the soft hydrophilic corneal contact lens is 0.872 mg/ml by means of calculation, that is: 2.2 mg/ml−1.328 mg/ml=0.872 mg/ml.

In one further embodiment, the operation that the soft hydrophilic corneal contact lens incubated in the artificial tear solution is placed into the protein extraction solution, and the protein is separated from the soft hydrophilic corneal contact lens through the protein extraction solution specifically comprises: 1 ml of the protein extraction solution is placed into the centrifuge tube, the soft hydrophilic corneal contact lens is placed into the centrifuge tube, the soft hydrophilic corneal contact lens is subjected to vibration cleaning in the centrifuge tube, and the adsorbed protein on the soft hydrophilic corneal contact lens is separated from the soft hydrophilic corneal contact lens. The protein concentration in the protein extraction solution is detected by means of the micro ultraviolet spectrophotometer to obtain the concentration value of the adsorbed protein on the soft hydrophilic corneal contact lens. For example, the concentration value of the adsorbed protein on the soft hydrophilic corneal contact lens is 0.805 mg/ml through detection. According to a concept that the mass equals to the product of the concentration and the volume, the content value of the adsorbed protein on the soft hydrophilic corneal contact lens may be calculated through the obtained concentration value of the adsorbed protein on the soft hydrophilic corneal contact lens and the volume of the protein extraction solution. That is, the product of the concentration value of the adsorbed protein on the soft hydrophilic corneal contact lens and the volume of the protein extraction solution is the content of the adsorbed protein on the soft hydrophilic corneal contact lens.

In one further embodiment, the method further comprises: obtaining an elution rate of the protein extraction solution on the protein by means of calculation based on the obtained concentration value of the adsorbed protein on the soft hydrophilic corneal contact lens and the theoretical concentration value of the adsorbed protein on the soft hydrophilic corneal contact lens.

Specifically, the elution rate of the protein extraction solution on the protein is calculated by means of a ratio of the concentration value (0.805 mg/ml) of the adsorbed protein on the soft hydrophilic corneal contact lens to the theoretical concentration value (0.872 mg/ml) of the adsorbed protein on the soft hydrophilic corneal contact lens. For example, the elution rate of the protein extraction solution on the protein is 92.3% by means of calculation. That is, 0.805 mg/ml÷0.872 mg/ml=92.3%.

In one embodiment, the soft hydrophilic corneal contact lens may adsorb a certain content of tear protein in manners of being worn by human eyes, being soaked by artificial tear solution, etc.

In one embodiment, 1 ml or 4 ml of the protein extraction solution (50 parts of acetonitrile, 50 parts of pure water and 0.2 part of 100% trifluoroacetic acid solution) may be taken to sufficiently dissolve the protein on the soft hydrophilic corneal contact lens which has adsorbed the tear protein, and is vibrated at a normal temperature for 24 hours for further dissolution, and the content of the protein extracted from the protein extraction solution may also be detected by a spectrophotometric method.

The present invention provides a method for effectively measuring the tear protein content of a soft hydrophilic corneal contact lens. Compared with the prior art, the present invention may solve the problem that the specific content of the adsorbed tear protein of the soft hydrophilic corneal contact lens is difficult to measure. The present invention separates the protein from the soft hydrophilic corneal contact lens through the protein extraction solution. The protein extraction solution may be a solution mixed by acetonitrile, pure water and trifluoroacetic acid, and the protein extraction solution does not take a reaction with a material of the soft hydrophilic corneal contact lens, and does not influence the measuring value of the protein. Therefore, the soft hydrophilic corneal contact lens incubated in the artificial tear solution may be used as a detection sample to be placed into the protein extraction solution for protein extraction and separation through vibration. Then, the protein concentration in the protein extraction solution is detected by means of the micro ultraviolet spectrophotometer, and the content value of the adsorbed protein on the soft hydrophilic corneal contact lens may be obtained by means of simple calculation on the protein concentration. Therefore, the specific content of the adsorbed tear protein on the soft hydrophilic corneal contact lens can be obtained by the method of the present invention. Further, the elution rate of the protein extraction solution on the protein may also be obtained by means of experiment detection calculation. Experiment results show that by using this method, the elution rate of the adsorbed tear protein on the soft hydrophilic corneal contact lens is higher than 90%.

In the description of this specification, the description of the reference terms "an embodiment", "some embodiments", "an example", "a specific example", "some examples" and the like means that specific features, structures, materials or characteristics described in combination with the embodiment(s) or example(s) are comprised in at least one embodiment or example of the present invention. In this specification, schematic descriptions of the foregoing terms are not necessarily directed at a same embodiment or example. In addition, the described specific features, structures, materials, or characteristics may be combined in a proper manner in any one or more of the embodiments or examples. In addition, those in the art may combine different embodiments or examples described in this specification.

Although the examples of the present invention have been shown and described above, it can be understood that, the foregoing embodiments are exemplary and should not be understood as limitation to the present invention. Those of ordinary skill in the art can make changes, modifications and variations to the foregoing examples within the scope of the present invention.

The above are only preferred embodiments of the present invention and are not intended to limit the present invention. Any modification, equivalent replacement, or improvement made within the spirit and principle of the present invention shall be comprised in the protection scope of the present invention.

What is claimed is:

1. A method for effectively measuring a tear protein content of a soft hydrophilic corneal contact lens, comprising:

preparing the soft hydrophilic corneal contact lens with adsorbed protein on its surface, comprising:

preparing an artificial tear solution, incubating the soft hydrophilic corneal contact lens in the artificial tear solution at a constant temperature, and taking out the soft hydrophilic corneal contact lens from the artificial tear solution after completion of incubation, wherein incubating the soft hydrophilic corneal contact lens in the artificial tear solution at a constant temperature comprises:

placing 1 ml of the artificial tear solution into a centrifuge tube, placing an unused soft hydrophilic corneal contact lens into the artificial tear solution for constant temperature incubation at 37° C. for 1 day, and taking out the soft hydrophilic corneal contact lens to obtain the soft hydrophilic corneal contact lens with protein adsorbed on its surface;

detecting a remaining protein concentration in the artificial tear solution by means of the micro ultraviolet spectrophotometer to obtain a remaining protein concentration value after the soft hydrophilic corneal contact lens is taken out from the artificial tear solution; and calculating a theoretical concentration value of the adsorbed protein on the soft hydrophilic corneal contact lens based on an original protein concentration value and the remaining protein concentration value in the artificial tear solution, comprising:

obtaining the theoretical concentration value of the adsorbed protein on the soft hydrophilic corneal contact lens by subtracting the obtained remaining protein concentration value from the original protein concentration value in the prepared artificial tear solution, wherein the original protein concentration value in the artificial tear solution is 2.2 mg/ml, the remaining protein concentration value is 1.328 mg/ml through detection, the theoretical concentration value of the adsorbed protein on the soft hydrophilic corneal contact lens is 0.872 mg/ml by means of calculation;

preparing a protein extraction solution by mixing acetonitrile, pure water and trifluoroacetic acid, wherein the protein extraction solution consists of 50 parts of acetonitrile, 50 parts of pure water and 0.2 part of 100% trifluoroacetic acid;

placing the soft hydrophilic corneal contact lens with protein adsorbed on its surface into the protein extraction solution so that the protein extraction solution separates the protein from the soft hydrophilic corneal contact lens, comprising:

placing 1 ml of the protein extraction solution into the centrifuge tube, and placing the soft hydrophilic corneal contact lens into the centrifuge tube for vibration cleaning to separate the adsorbed protein on the soft hydrophilic corneal contact lens from the soft hydrophilic corneal contact lens, wherein the protein concentration in the protein extraction solution is detected by means of the micro ultraviolet spectrophotometer to obtain the concentration value of the adsorbed protein on the soft hydrophilic corneal contact lens which is 0.805 mg/ml through detection; and the content value of the adsorbed protein on the soft hydrophilic corneal contact lens is calculated by means of the obtained concentration value of the adsorbed protein on the soft hydrophilic corneal contact lens;

US 12,631,552 B2

9 taking out the soft hydrophilic corneal contact lens from the protein extraction solution; detecting a protein concentration in the protein extraction solution by a micro ultraviolet spectrophotometer to obtain a concentration value of adsorbed protein on the soft hydrophilic corneal contact lens; and calculating a content value of the adsorbed protein on the soft hydrophilic corneal contact lens based on the concentration value of the adsorbed protein on the soft hydrophilic corneal contact lens and a volume of the protein extraction solution.

2. The method according to claim 1, further comprising:

calculating an elution rate of the protein extraction solution on the protein based on the obtained concentration value of the adsorbed protein on the soft hydrophilic corneal contact lens and the theoretical concentration value of the adsorbed protein on the soft hydrophilic corneal contact lens.

3. The method according to claim 2, wherein the calculating an elution rate of the protein extraction solution on the protein based on the obtained concentration value of the adsorbed protein on the soft hydrophilic corneal contact lens and the theoretical concentration value of the adsorbed protein on the soft hydrophilic corneal contact lens comprises:

obtaining the elution rate of the protein extraction solution on the protein by means of a ratio of the concentration value of the adsorbed protein on the soft hydrophilic corneal contact lens to the theoretical concentration value of the adsorbed protein on the soft hydrophilic corneal contact lens, wherein the elution rate of the protein extraction solution on the protein is 92.3% by means of calculation.

* * * * *